US009492814B2

(12) United States Patent
Irshad et al.

(10) Patent No.: US 9,492,814 B2
(45) Date of Patent: Nov. 15, 2016

(54) CATALYST FOR CONVERSION OF PROPYLENE TO PRODUCT COMPRISING A CARBOXYLIC ACID MOIETY

(71) Applicant: SAUDI BASIC INDUSTRIES CORPORATION, Riyadh (SA)

(72) Inventors: Zaheer Irshad, Riyadh (SA); Khalid Karim, Riyadh (SA)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 14/783,218

(22) PCT Filed: Apr. 7, 2014

(86) PCT No.: PCT/IB2014/060498
§ 371 (c)(1),
(2) Date: Oct. 8, 2015

(87) PCT Pub. No.: WO2014/167482
PCT Pub. Date: Oct. 16, 2014

(65) Prior Publication Data
US 2016/0051968 A1 Feb. 25, 2016

Related U.S. Application Data

(60) Provisional application No. 61/809,472, filed on Apr. 8, 2013.

(51) Int. Cl.
C07C 51/25 (2006.01)
B01J 27/057 (2006.01)
C01B 19/02 (2006.01)
B01J 37/03 (2006.01)
B01J 23/887 (2006.01)
C01B 19/00 (2006.01)
B01J 35/02 (2006.01)

(52) U.S. Cl.
CPC ......... B01J 27/0576 (2013.01); B01J 23/8877 (2013.01); B01J 37/031 (2013.01); C01B 19/002 (2013.01); C07C 51/252 (2013.01); B01J 35/023 (2013.01); B01J 2523/00 (2013.01)

(58) Field of Classification Search
CPC .................... C07C 51/252; B01J 23/6482
See application file for complete search history.

(56) References Cited

U.S. PATENT DOCUMENTS

| 3,654,354 | A | 4/1972 | Blanc |
| 4,536,483 | A | 8/1985 | Sasaki et al. |
| 4,757,038 | A | 7/1988 | Sasaki et al. |
| 4,792,620 | A * | 12/1988 | Paulik ................. B01J 31/0231 560/232 |
| 5,017,542 | A | 5/1991 | Martan et al. |
| 5,132,269 | A | 7/1992 | Sasaki et al. |
| 5,198,580 | A | 3/1993 | Bartek et al. |
| 5,235,088 | A | 8/1993 | Paparizos et al. |
| 5,336,651 | A | 8/1994 | Yoshimoto et al. |
| 6,080,882 | A | 6/2000 | Midorikawa et al. |
| 6,114,278 | A * | 9/2000 | Karim ................. B01J 23/62 502/240 |
| 6,646,158 | B1 | 11/2003 | Karim et al. |
| 7,229,946 | B2 | 6/2007 | Hazin et al. |
| 7,777,082 | B2 | 8/2010 | Petzoldt et al. |
| 7,807,853 | B2 | 10/2010 | Dieterle et al. |
| 2002/0115879 | A1 | 8/2002 | Hinago et al. |
| 2003/0088118 | A1 | 5/2003 | Komada et al. |
| 2005/0054869 | A1 | 3/2005 | Lugmair et al. |
| 2005/0065026 | A1 | 3/2005 | Okubo |
| 2005/0272952 | A1 | 12/2005 | Cremer et al. |
| 2006/0047137 | A1 | 3/2006 | Tu et al. |
| 2006/0183941 | A1 | 8/2006 | Dubois et al. |
| 2006/0235238 | A1 | 10/2006 | Komada et al. |
| 2006/0293538 | A1 | 12/2006 | Dubois et al. |
| 2007/0161767 | A1 | 7/2007 | Tu et al. |
| 2008/0139844 | A1 | 6/2008 | Dubois et al. |
| 2008/0194871 | A1 | 8/2008 | Dubois et al. |

FOREIGN PATENT DOCUMENTS

| CN | 1472009 A | 2/2004 |
| CN | 101279283 A | 10/2008 |
| CN | 102039143 A | 5/2011 |
| CN | 102049313 A | 5/2011 |
| CN | 102247862 A | 11/2011 |
| CN | 102247863 A | 11/2011 |

(Continued)

OTHER PUBLICATIONS

White et al,Basic Energy Sciences Advisory Committee Subpanel Workshop Report, Opportunities for Catalysis in the 21st Century, 2002, pp. 1-47.*
Norskov et al, Nature Chemistry, Towards the Computational Design of Solid Catalysts, 2009, 1, pp. 37-46.*
Chinese Patent No. 102049313; Date of Publication: May 11, 2011; Abstract Only, 1 page.
Chinese Patent No. 102247862; Date of Publication: Nov. 23, 2011; Abstract Only, 2 pages.
Chinese Patent No. 102247863; Date of Publication: Nov. 23, 2011; Abstract Only, 1 page.
French Patent No. 2397229; Date of Publication: Feb. 9, 1979; Abstract Only, 1 page.

(Continued)

Primary Examiner — Paul A Zucker
(74) Attorney, Agent, or Firm — Cantor Colburn LLP

(57) ABSTRACT

In accordance with the invention, there is provided a novel catalyst composition comprising MoVGaPdNbXY, wherein X comprises La, Te, Ge, Zn, In, or W; and Y comprises Al or Si; wherein Mo, V, Ga, Pd, Nb, La, Te, Ge, Zn, In, W, Al, or Si are optionally present in combination with oxygen; wherein the catalyst does not comprise an additional element that acts as a catalyst in the conversion of a propylene to the product. Also, disclosed is a method for the conversion of a propylene to a carboxylic acid moiety by contacting the propylene with the disclosed catalyst.

18 Claims, No Drawings

(56) References Cited

FOREIGN PATENT DOCUMENTS

| | | |
|---|---|---|
| EP | 1192982 A1 | 4/2002 |
| EP | 1574253 A2 | 9/2005 |
| EP | 1935868 A1 | 6/2008 |
| EP | 2075243 A1 | 7/2009 |
| FR | 2397229 A1 | 2/1979 |
| GB | 532676 | 1/1941 |
| JP | H04298235 A | 10/1992 |
| JP | H08150324 A | 6/1996 |
| JP | H10216519 A | 8/1998 |
| JP | 2000169420 A | 6/2000 |
| JP | 2001232207 A | 8/2001 |
| JP | 2001347165 A | 12/2001 |
| JP | 2002030028 A | 1/2002 |
| JP | 2004066024 A | 3/2004 |
| JP | 2004188341 A | 7/2004 |
| JP | 2005074377 A | 3/2005 |
| JP | 2005255572 A | 9/2005 |
| WO | 0029105 A1 | 5/2000 |
| WO | 0029106 A1 | 5/2000 |
| WO | 0170631 A1 | 9/2001 |
| WO | 0183103 A2 | 11/2001 |
| WO | 02062737 A2 | 8/2002 |
| WO | 02087751 A1 | 11/2002 |
| WO | 03039745 A1 | 5/2003 |
| WO | 2006058998 A2 | 6/2006 |
| WO | 2007074044 A1 | 7/2007 |
| WO | 2007118870 A2 | 10/2007 |
| WO | 2008068332 A1 | 6/2008 |
| WO | 2008152952 A1 | 12/2008 |
| WO | 2012101526 A1 | 8/2012 |

OTHER PUBLICATIONS

International Search Report for International Application No. PCT/IB2014/060498; Date of Mailing; Jul. 21, 2014; 5 pages.
Japanese Patent No. 2000169420; Date of Publication: Jun. 20, 2000; Abstract Only; 2 pages.
Japanese Patent No. 2001232207; Date of Publication: Aug. 28, 2001; Abstract Only, 1 page.
Japanese Patent No. 2001347165; Date of Publication: Dec. 18, 2001; Abstract Only, 1 page.
Japanese Patent No. 2002030028; Date of Publication: Jan. 29, 2002; Abstract Only, 1 page.
Japanese Patent No. 2004066024; Date of Publication: Mar. 4, 2004; Abstract Only, 1 page.
Japanese Patent No. 2004188341; Date of Publication: Jul. 8, 2004; Abstract Only, 1 page.
Japanese Patent No. 2005074377; Date of Publication: Mar. 24, 2005; Abstract Only, 1 page.
Japanese Patent No. H04298235; Date of Publication: Oct. 22, 1992; Abstract Only, 2 pages.
Japanese Patent No. H10216519; Date of Publication; Aug. 18, 1998; Abstract Only, 1 page.
Written Opinion of the International Searching Authority for International Application No. PCT/IB2014/060498; Date of Mailing: Jul. 21, 2014; 6 pages.
Botella P. et al. "Selective oxidation of C3-C4 olefins over Mo-containing catalysts with tetragonal tungsten bronze structure", Catalysis Today, 2009, vol. 141, pp. 311-316.
Chinese Patent No. 101279283; Date of Publication: Oct. 8, 2008; Abstract Only, 2 pages.
Chinese Patent No. 102039143; Date of Publication: May 4, 2011; Abstract Only, 2 pages.
Chinese Patent No. 1472009; Date of Publication: Feb. 4, 2004; Abstract Only, 1 page.
Ivars F. et al. "Influence of gel composition in the synthesis of MoVTeNb catalysts over their catalytic performance in partial propane and propylene oxidation." Catalysis Today, 2010, vol. 149, pp. 260-266.
Japanese Patent No. 2005255572; Date of Publication: Sep. 22, 2005; Abstract Only, 1 page.
Japanese Patent No. H8150324; Date of Publication: Jun. 1, 1996; Abstract Only; 2 pages.
Song Z. et al. "Gas-phase epoxidation of propylene through radicals generated by silica-supported molybdenum oxide." Applied Catalysis, 2007, vol. 316, pp. 142-151.
Vitry, D. et al. "Mo—V—Te—(Nb)—O mixed metal oxides prepared by hydrothermal synthesis for catalytic selective oxidations of propane and propene to acrylic acid." Applied Catalysis A: General 2003, vol. 251, pp. 411-424.
Yoshida, H. et al. "Screening Study of Silica-Supported Catalysts for Photoepoxidation of Propene by Molecular Oxygen", Journal of Catalysis, Sep. 2000, vol. 194, Issue 2, pp. 364-372.

* cited by examiner

CATALYST FOR CONVERSION OF PROPYLENE TO PRODUCT COMPRISING A CARBOXYLIC ACID MOIETY

This is the U.S. national stage of PCT Application No. PCT/IB2014/060498, filed on Apr. 7, 2014, the disclosure of which is incorporated herein by reference. Priority under 35 U.S.C. §119(a) and 35 U.S.C. §365(b) is claimed from U.S. Application Ser. No. 61/809,472, filed Apr. 8, 2013, the disclosure of which is incorporated herein by reference.

BACKGROUND OF THE INVENTION

Previous research has involved a two-stage vapor phase oxidation of propylene to produce acrylic acid. However, there is no single stage process that exists for the catalytic oxidation of propylene to acrylic acid. The one-stage production of acrylic acid from propylene would be attractive because of the technical problems that could be avoided, such as deactivation of a stage II catalyst, presence of partially oxidized material, and acrolein in the product mixture. As such, it is desirable to prepare a catalyst that can selectively produce acrylic acid or other conversions of propylene comprising a carboxylic acid in high yield at the desired temperature from propylene, without producing significant amounts of acrolein.

SUMMARY OF THE INVENTION

According to one aspect of the invention, a catalyst is disclosed for the conversion of a propylene to a product comprising a carboxylic acid moiety, wherein the catalyst comprises:

$MoVGaPdNbXY$, wherein
X comprises La, Te, Ge, Zn, In, or W; and
Y comprises Al or Si; and
one or more of Mo, V, Ga, Pd, Nb, La, Te, Ge, Zn, In, W, Al, and/or Si are optionally present in combination with oxygen;
wherein the catalyst does not comprise an additional element that acts as a catalyst in the conversion of the propylene to the product.

According to one aspect of the invention, a catalyst for the conversion of a propylene to a product comprising a carboxylic acid moiety, wherein the catalyst consists essentially of:

$MoVGaPdNbXY$, wherein
X comprises La, Te, Ge, Zn, In, or W; and
Y comprises Al or Si;
wherein
one or more Mo, V, Ga, Pd, Nb, La, Te, Ge, Zn, In, W, Al, and/or Si are optionally present in combination with oxygen.

According to one aspect of the invention, a method for the conversion of a propylene to a product comprising a carboxylic acid moiety, wherein the method comprises: contacting the propylene with a catalyst, wherein the catalyst comprises:

$MoVGaPdNbXY$, wherein
X comprises La, Te, Ge, Zn, In, or W; and
Y comprises Al or Si;
wherein
one or more Mo, V, Ga, Pd, Nb, La, Te, Ge, Zn, In, W, Al, and/or Si are optionally present in combination with oxygen.

Other advantages will be set forth in part in the description which follows, or can be learned by practice. The advantages will be realized and attained by means of the elements and combinations particularly pointed out in the appended claims. It is to be understood that both the foregoing general description and the following detailed description are exemplary and explanatory only and are not restrictive, as claimed.

DETAILED DESCRIPTION OF THE INVENTION

Other aspects, as well as aspects, features and advantages of the present invention will become apparent from a study of the present specification, including the claims and specific examples.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used herein, nomenclature for compounds, including organic compounds, can be given using common names, IUPAC, IUBMB, or CAS recommendations for nomenclature.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or can not occur, and that the description includes instances where said event or circumstance occurs and instances where it does not.

Unless otherwise expressly defined otherwise, symbols that represent the chemical elements are used. For example, Mo represents molybdenum, V represents vanadium, Ga represents gallium, etc.

In defining various terms, "X and Y" are used herein as generic symbols to represent various specific elements. When they are defined to be certain elements in one instance, they can, in another instance, be defined as some other elements.

The term "olefin", as used herein, refers to any unsaturated hydrocarbon containing one or more pairs of carbon atoms linked by a double bond. An example of an olefin is propylene, or $HC=CH-CH_3$.

The term "acrolein" as used herein is represented by the formula $HC=C-C(O)H$. Throughout this specification "C(O)" is a short hand notation for a carbonyl group, i.e., $C=O$.

The term "carboxylic acid" as used herein is represented by the formula $C(O)OH$.

The terms "halo," "halogen," or "halide," as used herein can be used interchangeably and refer to F, Cl, Br, or I.

The term "stable," as used herein, refers to compounds that are not substantially altered when subjected to conditions to allow for their production, detection, and, in certain aspects, their recovery, purification, and use for one or more of the purposes disclosed herein.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The following abbreviations are used herein.
° C. degrees Celsius
h hour(s)
$h^{-1}$ reciprocal hour(s)
m meter(s)
mL milliliter(s)
mm millimeter(s)
psia pounds per square inch Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

A. CATALYST

According to one aspect of the invention, a catalyst is disclosed for the conversion of a propylene to a product comprising a carboxylic acid moiety, wherein the catalyst comprises:

MoVGaPdNbXY, wherein
X comprises La, Te, Ge, Zn, In, or W; and
Y comprises Al or Si; and
one or more Mo, V, Ga, Pd, Nb, La, Te, Ge, Zn, In, W, Al, and/or Si are optionally present in combination with oxygen;
wherein the catalyst does not comprise an additional element that acts as a catalyst in the conversion of a propylene to the product.

According to a further aspect of the invention, a catalyst is disclosed for the conversion of a propylene to a product comprising a carboxylic acid moiety, wherein the catalyst consists essentially of:

MoVGaPdNbXY, wherein
X comprises La, Te, Ge, Zn, In, or W; and
Y comprises Al or Si; and
one or more Mo, V, Ga, Pd, Nb, La, Te, Ge, Zn, In, W, Al, and/or Si are optionally present in combination with oxygen.

According to a further aspect of the invention, a catalyst is disclosed for the conversion of a propylene to a product comprising a carboxylic acid moiety, wherein the catalyst consists of:

MoVGaPdNbXY, wherein
X comprises La, Te, Ge, Zn, In, or W; and
Y comprises Al or Si; and
one or more Mo, V, Ga, Pd, Nb, La, Te, Ge, Zn, In, W, Al, and/or Si are optionally present in combination with oxygen.

According to another aspect of the invention, a catalyst is disclosed wherein the catalyst comprises:

$Mo_aV_bGa_cPd_dNb_eX_fY_g$, wherein
a is 1;
b is present in an amount that ranges from 0.01 to 0.9;
c is present in an amount that ranges from greater than 0 to 0.2;
d is present in an amount that ranges from 0.0000001 to 0.2;
e is present in an amount that ranges from greater than 0 to 0.2;
f is present in an amount that ranges from greater than 0 to 0.8; and
g is present in an amount that ranges from greater than 0.5 to 0.9;
wherein the numerical values of a, b, c, d, e, f, and g represent the relative gram-atom ratios of the elements in the catalyst.

In one aspect, the molybdenum is introduced into the catalyst in a solution in the form of an ammonium salt, such as ammonium paramolybdate, or as organic acid salts of molybdenum; such as acetate, oxalate, mandelate, and glycolate. In another aspect, a partially water soluble molybdenum compound can be used, such as molybdenum oxide, molybdic acid, or a chloride of molybdenum. In another aspect, the molybdenum can be added in any form, except its elemental form.

In one aspect, the molybdenum is present in an amount of 1 for the relative gram-atom ratio of the element in the catalyst.

In another aspect, the vanadium is introduced into the catalyst in a solution in the form of an ammonium salt, such as ammonium metavanadate and ammonium decavanadate, or an organic salt of vanadium; such as acetate, oxalate, and tartrate. In a further aspect, a partially water soluble vanadium compound such as vanadium oxide, and a sulfate of vanadium can also be used. To achieve a complete solubility, a certain amount of oxalic or tartaric acid can be added. In another aspect, the vanadium can be added in any form, except its elemental form.

In one aspect, the vanadium is present in an amount that ranges from 0.01 to 0.90 for the relative gram-atom ratio of the element in the catalyst, including the exemplary values of 0.02, 0.03, 0.04, 0.05, 0.06, 0.07, 0.08, 0.09, 0.10, 0.20, 0.30, 0.40, 0.50, 0.60, 0.70, and 0.80. In still further aspects, the relative gram-atom ratio of vanadium in the catalyst can be in a range derived from any two of the above listed exemplary relative gram-atom ratio of vanadium in the catalyst. For example, the vanadium is present in an amount that ranges from 0.03 to 0.90 for the relative gram-atom ratio of the element in the catalyst. Further for example, the vanadium is present in an amount that ranges from 0.10 to 0.90 for the relative gram-atom ratio of the element in the catalyst.

In a further aspect, the gallium is introduced into the catalyst in a solution in the form of a salt of gallium such as oxide, chloride, nitrate, and the like. In another aspect, the galliuim can be added in any form, except its elemental form.

In one aspect, the gallium is present in an amount that ranges from greater than 0 to 0.2 for the relative gram-atom ratio of the element in the catalyst. In another aspect, the gallium is present in an amount that ranges 0.01 to 0.20 for the relative gram-atom ratio of the element in the catalyst, including the exemplary values of 0.02, 0.03, 0.04, 0.05, 0.06, 0.07, 0.08, 0.09, 0.10, 0.11, 0.12, 0.13, 0.14, 0.15, 0.16, 0.17, 0.18, and 0.19. In still further aspects, the relative gram-atom ratio of gallium in the catalyst can be in a range derived from any two of the above listed exemplary relative gram-atom ratio of gallium in the catalyst. For example, gallium is present in an amount that ranges from 0.03 to 0.15 for the relative gram-atom ratio of the element in the catalyst. Further for example, the gallium is present in an amount that ranges from 0.10 to 0.19 for the relative gram-atom ratio of the element in the catalyst.

In an even further aspect, the palladium is introduced into the catalyst in a solution in the form of Pd on activated charcoal, alumina, or as a solution of a salt of palladium; such as acetate, chloride, or nitrate, and the like. In another aspect, the palladium can be added in any form, except its elemental form.

In one aspect, the palladium is present in an amount that ranges from 0.0000001 to 0.20 for the relative gram-atom ratio of the element in the catalyst, including the exemplary values of 0.000001, 0.00001, 0.0001, 0.001, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, and 0.19. In still further aspects, the relative gram-atom ratio of palladium in the catalyst can be in a range derived from any two of the above listed exemplary relative gram-atom ratio of palladium in the catalyst. For example, the palladium is present in an amount that ranges from 0.00001 to 0.15 for the relative gram-atom ratio of the element in the catalyst. Further for example, the palladium is present in an amount that ranges from 0.10 to 0.19 for the relative gram-atom ratio of the element in the catalyst.

In a yet further aspect, the niobium is used in the form of an oxalate or a hydrate of oxide. Other sources of this metal in soluble form include a compound in which the metal is coordinated, bonded or complexed to a beta-diketonate, carboxylic acid, an amine, an alcohol, or an alkanolamine. In another aspect, the niobium can be added in any form, except its elemental form.

In one aspect, the niobium is present in an amount that ranges from greater than 0 to 0.20 for the relative gram-atom ratio of the element in the catalyst. In another aspect, the niobium is present in an amount that ranges 0.01 to 0.20 for the relative gram-atom ratio of the element in the catalyst, including the exemplary values of 0.02, 0.03, 0.04, 0.05, 0.06, 0.07, 0.08, 0.09, 0.10, 0.11, 0.12, 0.13, 0.14, 0.15, 0.16, 0.17, 0.18, and 0.19. In still further aspects, the relative gram-atom ratio of niobium in the catalyst can be in a range derived from any two of the above listed exemplary relative gram-atom ratio of niobium in the catalyst. For example, the niobium is present in an amount that ranges from 0.015 to 0.18 for the relative gram-atom ratio of the element in the catalyst. Further for example, the niobium is present in an amount that ranges from 0.02 to 0.17 for the relative gram-atom ratio of the element in the catalyst.

In one aspect, the X in the catalyst comprises lanthanum, tellurium, germanium, zinc, indium or tungsten. In another aspect, the catalyst comprises only a single element of those listed as the elements under X. In a further aspect, the catalyst comprises a combination of the elements under X. In an even further aspect, the lanthanum, tellurium, germanium, zinc, indium, or tungsten can be introduced into the catalyst in a solution in the form of a salt of an oxide, acetate, chloride, or nitrate, or the like. In another aspect, the lanthanum, tellurium, germanium, zinc, indium, or tungsten can be added in any form, except their elemental form.

In one aspect, the X is present in an amount that ranges from greater than 0 to 0.80 for the relative gram-atom ratio of the element in the catalyst. In another aspect, the X is present in an amount that ranges 0.01 to 0.80 for the relative gram-atom ratio of the element in the catalyst, including the exemplary values of 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, and 0.75. In still further aspects, the relative gram-atom ratio of X in the catalyst can be in a range derived from any two of the above listed exemplary gram-atom ratio of X in the catalyst. For example, the X is present in an amount that ranges from 0.10 to 0.75 for the relative gram-atom ratio of the element in the catalyst. Further for example, the X is present in an amount that ranges from 0.20 to 0.70 for the relative gram-atom ratio of the element in the catalyst. In one aspect, each element under X can be present in the ranges above. In another aspect, the total amount of the elements under X can be present in the ranges above.

In one aspect, the Y in the catalyst comprises aluminum or silica, or a combination thereof. In another aspect, the catalyst comprises only a single element of those listed as the elements under Y. In a further aspect, the catalyst comprises a combination of the elements under Y. In a further aspect, the aluminum or silica can be introduced into the solution in the form of a salt of an oxide, acetate, chloride, or nitrate, or the like. In another aspect, the aluminum or silica can be added in any form, except their elemental form.

In one aspect, the Y is present in an amount that ranges from greater than 0.50 to 0.90 for the relative gram-atom ratio of the element in the catalyst. In another aspect, the Y is present in an amount that ranges 0.51 to 0.90 for the relative gram-atom ratio of the element in the catalyst, including the exemplary values of 0.52, 0.53, 0.54, 0.55, 0.56, 0.57, 0.58, 0.59, 0.60, 0.65, 0.70, 0.75, 0.80, and 0.85. In still further aspects, the relative gram-atom ratio of Y in the catalyst can be in a range derived from any two of the above listed exemplary relative gram-atom ratio of Y in the catalyst. For example, the Y is present in an amount that ranges from 0.55 to 0.80 for the relative gram-atom ratio of the element in the catalyst. Further for example, the Y is present in an amount that ranges from 0.60 to 0.75 for the relative gram-atom ratio of the element in the catalyst. In one aspect, each element under Y can be present in the ranges above. In another aspect, the total amount of the elements under Y can be present in the ranges above.

In one aspect, the catalyst does not comprise an additional element that acts as a catalyst in the conversion of propylene to the product. That is, other elements can be present, but they do not provide any appreciable catalyst activity. In a further aspect, the additional element is a metal. In another aspect, the additional element is a nonmetal. In a yet further aspect, the additional element is Sb or Cs, or a combination thereof. In another aspect, the catalyst does not comprise an additional metal. In an even further aspect, the catalyst does not comprise Sb or Cs, or a combination thereof.

The catalyst of the invention can be used with or without a support. In one aspect, the catalyst is present on a support. Suitable supports for the catalyst can include, but are not limited to, alumina, silica, titania, zirconia, zeolites, silicon carbide, Mo carbide, molecular sieves and other micro/nonporous materials, and mixtures thereof.

In one aspect, the support material is present in an amount in the range of from 50 wt % to 90 wt % of the total catalyst composition, including exemplary values of 55 wt %, 60 wt %, 65 wt %, 70 wt %, 75 wt %, 80 wt %, and 85 wt %. In still further aspects, the weight percentage can be in a range derived from any two of the above listed exemplary weight percentages. For example, the support material is present in an amount in the range of from 55 wt % to 85 wt %. Further for example, the support material is present in an amount in the range of from 60 wt % to 80 wt %.

One aspect of the invention relates to the method of making the catalyst. The choice of the compounds used as well as the specific procedures followed in preparing a catalyst can have an effect on the performance of a catalyst. The elements of the catalyst composition can be in combination with oxygen as oxides.

In one aspect, the catalyst is prepared from a solution of soluble compounds (salts, complexes or other compounds) of each of the metals. In one aspect, the solution is an aqueous system having a pH of about 1 to about 10, including exemplary values of 2, 3, 4, 5, 6, 7, 8, and 9. In still further aspects, the solution can have a pH in a range derived from any two of the above listed exemplary values. For example, the solution can have a pH in a range of from 1 to 7. In one aspect, the pH is measured at a temperature of from about 30° C. to about 100° C.

Generally, a mixture of compounds containing the elements is prepared by dissolving sufficient quantities of soluble compounds and dispersing the insoluble compounds so as to provide the desired gram-atom ratios of the elements in the catalyst composition. The catalyst composition is then prepared by removing the water and/or other solvent from the mixture of the compounds in the solution system. The dried catalyst is calcined by heating to the desired temperature in air or oxygen for the desired period of time to produce the desired catalyst composition.

In one aspect, the dried catalyst is calcined by heating to a temperature from about 250° C. to about 450° C. in air or oxygen, including exemplary values of 275° C., 300° C., 325° C., 350° C., 375° C., 400° C., and 425° C. In still further aspects, the temperature can be in a range derived from any two of the above listed exemplary temperatures. For example, the temperature can range from 275° C. to 425° C. or from 300° C. to 400° C.

In another aspect, the catalyst is dried for a period of time ranging from about one hour to about 16 hours to produce the desired catalyst composition, including exemplary values of 1.5 hr, 2 hr, 3 hr, 4 hr, 5 hr, 6 hr, 7 hr, 8 hr, 9 hr, 10 hr, 11 hr, 12 hr, 13 hr, 14 hr, and 15 hr. In still further aspects, the time can be in a range derived from any two of the above exemplary times. For example, the catalyst can be dried for a period time ranging from 1.5 hr to 15 hr. Further for example, the catalyst can be dried for a period of time ranging from 2 hr to 13 hr.

In one aspect, the disclosed catalyst can be used in the disclosed reaction and methods.

B. REACTION

The catalyst converts a propylene to a product. In one aspect, other alkanes or alkenes can be present as an impurity in the feed stream. The product comprises a carboxylic acid moiety. In one aspect, the product comprises acetic acid, acrylic acid, or propanoic acid, or a combination thereof. In a further aspect, the product does not comprise substantially any acrolein. In an even further aspect, the product does not comprise acrolein.

In a further aspect, the catalyst converts the propylene to the product comprising a carboxylic acid moiety in a single stage.

In one aspect, the catalyst can produce a reaction with high conversion and selectivity to acrylic acid. In another aspect, the catalyst can produce a reaction with high conversion and selectivity to acrylic acid without producing acrolein in the product. In a further aspect, the catalyst has high thermal stability.

In one aspect, the disclosed reaction can be performed with the disclosed catalysts and using the disclosed methods.

C. METHODS

In one aspect, disclosed is a method for the conversion of a propylene to a product comprising a carboxylic acid moiety, wherein the method comprises: contacting a propylene with a catalyst, wherein the catalyst comprises:

$Mo_a V_b Ga_b Pd_c Nb_d X_e Y_f$, wherein
X comprises La, Te, Ge, Zn, In, or W; and
Y comprises Al or Si;
wherein
one or more Mo, V, Ga, Pd, Nb, La, Te, Ge, Zn, In, W, Al, and/or Si are optionally present in combination with oxygen.

Another aspect of the invention relates to a method of using the inventive catalyst system for the high selectivity oxidation of propylene to a product. As used herein, the high selectivity oxidation means a reaction that leads to the product, rather than to $CO_2$ formation. In one aspect, the high selectivity oxidation leads to acrylic acid, rather than to $CO_2$ formation.

In one aspect, the method comprises a gas stream. The gas stream comprises various components to facilitate the reaction proceeding.

In one aspect, the gas stream comprises propylene. In another aspect, the gas stream comprises at least three volume percent of propylene based on the total volume of the gas stream. In an even further aspect, the gas stream comprises propylene in an amount ranging from 3% vol to 94.9% vol based on the total volume of the gas stream, including exemplary percent volume of 4% vol, 5% vol, 6% vol, 8% vol, 10% vol, 15% vol, 20% vol, 25% vol, 30% vol, 35% vol, 40% vol, 45% vol, 50% vol, 55% vol, 60% vol, 65% vol, 70% vol, 75% vol, 80% vol, 85% vol, 90% vol, and 94% vol. In still further aspects, the percent volume can be in a range derived from any two of the above exemplary percent volumes. For example, the gas stream comprises propylene in an amount ranging from 5% vol to 90% vol based on the total volume of the gas stream. Further for example, the gas stream comprises propylene in an amount ranging from 10% vol to 85% vol based on the total volume of the gas stream.

In another aspect, the gas stream further comprises nitrogen, argon, carbon dioxide, or water, or a combination thereof. In a further aspect, the water can take the form of steam.

In an even further aspect, the gas stream can comprise nitrogen, argon, carbon dioxide, or water, or combination thereof in an amount greater than 5% by volume based on the total volume of the gas stream. In a yet further aspect, the gas stream can comprise nitrogen, argon, carbon dioxide, or water, or a combination thereof in an amount ranging from 5% vol to 96.9% vol based on the total volume of the gas stream, including exemplary values of 7% vol, 10% vol, 15% vol, 20% vol, 25% vol, 30% vol, 35% vol, 40% vol, 45% vol, 50% vol, 55% vol, 60% vol, 65% vol, 70% vol, 75% vol, 80% vol, 85% vol, 90% vol, and 95% vol. In still further aspects, the percent volume can be in a range derived from any two of the above exemplary percent volumes. For example, the gas stream comprises nitrogen, argon, carbon dioxide, or water, or a combination thereof in an amount ranging from 15% vol to 70% vol based on the total volume of the gas stream. Further for example, the gas stream comprises nitrogen, argon, carbon dioxide, or water, or a combination thereof in an amount ranging from 10% vol to 85% vol based on the total volume of the gas stream.

In one aspect, the gas stream can further comprise oxygen. The source of oxygen can comprise air, pure oxygen, or oxygen enriched air, or a combination thereof. In one aspect, air is the source of oxygen in the feed. In another aspect, the source of oxygen is pure oxygen.

The gas stream can comprise oxygen in an amount ranging from 0.1% vol to 50% vol based on the total volume of the gas stream, including exemplary values of 0.5% vol, 1% vol, 5% vol, 10% vol, 15% vol, 20% vol, 25% vol, 30% vol, 35% vol, 40% vol, and 45% vol. In still further aspects, the percent volume can be in a range derived from any two of the above exemplary percent volumes. For example, the gas stream comprises oxygen in an amount ranging from 5% vol to 45% vol based on the total volume of the gas stream. Further for example, the gas stream comprises oxygen in an amount ranging from 10% vol to 40% vol based on the total volume of the gas stream.

In one aspect, the reaction mixture comprises about 0.01 mol to about 2.0 mol of molecular oxygen for every mole of propylene, including exemplary values of 0.02 mol, 0.03 mol, 0.04 mol, 0.05 mol, 0.06 mol, 0.07 mol, 0.08 mol, 0.09 mol, 0.1 mol, 0.2 mol, 0.3 mol, 0.4 mol, 0.5 mol, 0.6 mol, 0.7 mol, 0.8 mol, 0.9 mol, 1 mol, 1.1 mol, 1.2 mol, 1.3 mol, 1.4 mol, 1.5 mol, 1.6 mol, 1.7 mol, 1.8 mol, and 1.9 mol. In still further aspects, the moles of molecular oxygen can be in a range derived from any two of the above exemplary moles of molecular oxygen. For example, the reaction mixture comprises about 0.1 mol to 1.9 mol of molecular oxygen for every mole of propylene. Further for example, the reaction mixture comprises about 0.05 mol to 1.5 mol of molecular oxygen for every mole of propylene.

In another aspect, the reaction mixture comprises from 0 mol to 4.0 mol of water for every mole of propylene, including exemplary values of 0.1 mol, 0.2 mol, 0.3 mol, 0.4 mol, 0.5 mol, 0.6 mol, 0.7 mol, 0.8 mol, 0.9 mol, 1 mol, 1.2 mol, 1.4 mol, 1.6 mol, 1.8 mol, 2 mol, 2.2 mol, 2.4 mol, 2.6 mol, 2.8 mol, 3 mol, 3.2 mol, 3.4 mol, 3.6 mol, and 3.8 mol. In still further aspects, the moles of water can be in a range derived from any two of the above exemplary moles of water. For example, the reaction mixture comprises from 0.1 mol to 3.8 mol of water for every mole of propylene. Further for example, the reaction mixture comprises from 0.5 mol to 3.0 mol of water for every mole of propylene.

The ratio of propylene to oxygen can vary based on the desired conversion and the selectivity of the catalyst. In one aspect, the ratio of propylene to oxygen ranges from 1:5 to 5:1, including exemplary ratios of 2:5, 3:5, 4:5, 1:1, 2:1, 3:1, and 4:1. In still further aspects, the ratio of propylene to oxygen can be in a range derived from any two of the above exemplary ratios. For example, the ratio of propylene to oxygen ranges from 2:5 to 4:1. Further for example, the ratio of propylene to oxygen ranges from 3:5 to 3:1.

In one aspect, the argon, carbon dioxide, nitrogen, or water, or combination thereof can act as a reaction diluent. The ratio of propylene to the total amount of argon, carbon dioxide, nitrogen, or water, or a combination thereof, ranges from 1:5 to 1:1, including exemplary values of 1:4, 1:3, and 1:2. In still further aspects, the ratio of propylene to the total amount of argon, carbon dioxide, nitrogen, or water, or a combination thereof can be in a range derived from any two of the above exemplary ratios. For example, the ratio of propylene to the total amount of argon, carbon dioxide, nitrogen, or water, or a combination thereof, ranges from 1:4 to 1:2. Further for example, the ratio of propylene to the total amount of argon, carbon dioxide, nitrogen, or water, or a combination thereof, ranges from 1:3 to 1:1.

In another aspect, the water vapor can act as a reaction diluent and as a heat moderator for the reaction. It also can act as a desorption accelerator of the reaction product in the vapor phase oxidation reaction.

In a further aspect, the gas stream can further comprise helium, nitrogen, or carbon dioxide, or a combination thereof as a reaction diluent and/or a heat moderator.

The liquid products of the reaction can be separated from the unreacted feed hydrocarbons by condensation or scrubbing. In one aspect, the scrubbing can be performed by water or dilute acid.

In one aspect, the gas stream comprises various components. In another aspect, the gas stream components are uniformly admixed prior to being introduced into the reaction zone. In a further aspect, the gas stream components are not uniformly mixed prior to being introduced into the reaction zone.

In a yet further aspect, the gas stream components are preheated, individually or after being admixed, prior to being introduced into the reaction zone.

The reaction pressure can be initially provided by the feed of the gaseous reactant and diluent and after the reaction has commenced, can be maintained by the use of a suitable back-pressure controller placed on the reactor outlet stream. In one aspect, the reaction zone has a pressure in an amount ranging from 1 bar to 50 bar (0.1 MegaPascals (MPa) to 5 MPa, including exemplary pressures of 2 bar (0.2 MPa), 4 bar (0.4 MPa), 6 bar (0.6 MPa), 8 bar (0.8 MPa), 10 bar (1 MPa), 15 bar (1.5 MPa), 20 bar (2.0 MPa), 25 bar (2.5 MPa), 30 bar (3.0 MPa), 35 bar (3.5 MPa), 40 bar (4.0 MPa), and 45 bar (4.5 MPa). In still further aspects, the pressure can be in a range derived from any two of the above exemplary pressures. For example, the reaction zone has a pressure in an amount ranging from 1 bar to 45 bar (0.1 MPa to 4.5 MPa). Further for example, the reaction zone has a pressure in an amount ranging from 1 bar to 30 bar (0.1 MPa to 3.0 MPa).

The reaction temperature can be provided by placing the catalyst bed within a tubular converter having walls placed in a furnace heated to the desired reaction temperature. In one aspect, the reaction zone has a temperature in an amount ranging from 150° C. to about 450° C., including exemplary temperatures of 175° C., 200° C., 225° C., 250° C., 275° C., 300° C., 325° C., 350° C., 375° C., 400° C., and 425° C. In still further aspects, the temperature can be in a range from any two of the above exemplary temperatures. For example, the reaction zone has a temperature in an amount ranging from 175° C. to 425° C. Further for example, the reaction zone has a temperature in an amount ranging from 200° C. to 300° C.

The contact time is defined as the ratio between the apparent volume of the catalyst bed and the volume of the gaseous reaction mixture feed to the catalyst bed under the given reaction conditions in a unit. In one aspect, the reaction zone has a contact time between the reaction mixture and the catalyst in an amount ranging from 0.01 second to 100 seconds, including exemplary times of 0.05 sec, 0.08 sec, 0.1 sec, 0.4 sec, 0.6 sec, 0.8 sec, 1 sec, 5 sec, 10 sec, 15 sec, 20 sec, 25 sec, 30 sec, 35 sec, 40 sec, 45 sec, 50 sec, 55 sec, 60 sec, 65 sec, 70 sec, 75 sec, 80 sec, 85 sec, 90 sec, and 95 sec. In still further aspects, the contact time can be in a range from any two exemplary contact times. For example, the reaction zone has a contact time between the reaction mixture and the catalyst in an amount ranging from 0.05 sec to 95 sec. Further for example, the reaction zone has a contact time between the reaction mixture and the catalyst in an amount ranging from 1 sec to 80 sec. Even further for example, the reaction zone has a contact time between the reaction mixture and the catalyst in an amount ranging from 0.1 sec to 10 sec.

The space velocity is calculated by determining the total reactor outlet gas equivalent in liters of the total effluent evolved over a period of one hour divided by the liters of catalyst in the reactor. This room temperature volume is converted to the volume at 0° C. at 1 bar (0.1 MPa).

In one aspect, the reaction zone has a space hourly velocity in an amount ranging from 50 $h^{-1}$ to about 50,000 $h^{-1}$, including exemplary values of 100 $h^{-1}$, 150 $h^{-1}$, 200 $h^{-1}$, 250 $h^{-1}$, 300 $h^{-1}$, 400 $h^{-1}$, 500 $h^{-1}$, 1,000 $h^{-1}$, 2,000 $h^{-1}$, 3,000 $h^{-1}$, 3,500 $h^{-1}$, 4,000 $h^{-1}$, 4,500 $h^{-1}$, 5,000 $h^{-1}$, 6,000 $h^{-1}$, 7,000 $h^{-1}$, 8,000 $h^{-1}$, 9,000 $h^{-1}$, 10,000 $h^{-1}$, 11,000 $h^{-1}$, 12,000 $h^{-1}$, 13,000 $h^{-1}$, 14,000 $h^{-1}$, 15,000 $h^{-1}$, 16,000 $h^{-1}$, 17,000 $h^{-1}$, 18,000 $h^{-1}$, 19,000 $h^{-1}$, 20,000 $h^{-1}$, 21,000 $h^{-1}$, 22,000 $h^{-1}$, 23,000 $h^{-1}$, 25,000 $h^{-1}$, 27,000 $h^{-1}$, 30,000 $h^{-1}$, 33,000 $h^{-1}$, 35,000 $h^{-1}$, 37,000 $h^{-1}$, 40,000 $h^{-1}$, 43,000 $h^{-1}$, and 47,000 $h^{-1}$. In still further aspects, the space hourly velocity can be in a range chosen from any two exemplary values. For example, the reaction zone has a space hourly velocity in an amount ranging from 100 $h^{-1}$ to 10,000 $h^{-1}$.

Further for example, the reaction zone has a space hourly velocity in an amount ranging from 200 h$^{-1}$ to 3,000 h$^{-1}$.

The oxidation performed according to the invention can provide a selectivity to produce acrylic acid of at least about 50% per single pass through the reaction zone. In one aspect, the oxidation provided a selectivity to produce acrylic acid of at least about 70% per single pass through the reaction zone. In another aspect, the oxidation provides a selectivity to produce acrylic acid in an amount ranging from 50% to 99% per single pass through the reaction zone, including exemplary values 55%, 60%, 65%, 70%, 75%, 80%, 85%, 90%, 95%, and 97%. In still further aspects, the selectivity value can be in a range chosen from any two exemplary values. For example, the oxidation provides a selectivity to produce acrylic acid in an amount ranging from 70% to 99% per single pass through the reaction zone.

In one aspect of the invention, less than 1 wt % acrolein is formed in the product using the catalyst system. In another aspect, acrolein is formed in the product in an amount ranging from greater than 0 wt % to 1 wt % using the catalyst system. In another aspect, the product does not comprise substantially any acrolein. In yet another aspect, the product does not comprise any acrolein, that is no detectable acrolein is formed in the product using this catalyst system.

In one aspect, the method comprises a single stage process with a single catalyst. As used herein, a single stage process refers to a process wherein the oxygen and reactants are supplied as a single feed. In another aspect, the method does not comprise adding an additional catalyst. In a yet further aspect, the method does not comprise adding an additional catalyst to the single stage process.

In another aspect, the method comprises a multistage process. During a multistage process, the reactants can be added at various stages. Further, a multiple stage addition of oxygen or hydrocarbon to the reactor can be used and/or recycling of unreacted gases with purge mode can be applied to improve the overall productivity and/or yield of the desired products.

In one aspect, the disclosed method can be performed with the disclosed catalysts to produce the disclosed reaction.

In one aspect, the method avoids the problems of a conventional two stage process and/or using two catalysts, such as deactivation of a stage II catalyst, presence of partially oxidized material, and/or acrolein in the product mixture. In another aspect, the method has a lower capital investment by being a single stage process.

D. ASPECTS

The disclosed compositions and methods include at least the following aspects.

Aspect 1: A catalyst for the conversion of a propylene to a product comprising a carboxylic acid moiety, wherein the catalyst comprises:

MoVGaPdNbXY, wherein
   X comprises La, Te, Ge, Zn, In, or W; and
   Y comprises Al or Si;
wherein
   one or more Mo, V, Ga, Pd, Nb, La, Te, Ge, Zn, In, W, Al,
   and/or Si are optionally present in combination with oxygen;

wherein the catalyst does not comprise an additional element that acts as a catalyst in the conversion of the propylene to the product.

Aspect 2: The catalyst according to aspect 1, wherein the product does not comprise substantially any acrolein.

Aspect 3: The catalyst according to any of aspects 1 or 2, wherein the product does not comprise any acrolein.

Aspect 4: The catalyst according to any of aspects 1-3, wherein the additional element is a metal.

Aspect 5: The catalyst according to any of aspects 1-4, wherein the additional element comprises Sb or Cs, or a combination thereof.

Aspect 6: A catalyst for the conversion of a propylene to a product comprising a carboxylic acid moiety, wherein the catalyst consists of or consists essentially of:

MoVGaPdNbXY, wherein
   X comprises La, Te, Ge, Zn, In, or W; and
   Y comprises Al or Si;
wherein
   one or more Mo, V, Ga, Pd, Nb, La, Te, Ge, Zn, In, W, Al,
   and/or Si are optionally present in combination with oxygen.

Aspect 7: The catalyst according to any one of aspects 1-6, wherein the catalyst is present on a support.

Aspect 8: The catalyst according to any one of aspects 1-7, wherein the catalyst comprises:

$Mo_aV_bGa_cPd_dNb_eX_fY_g$ wherein a is 1; b is present in an amount that ranges from 0.01 to 0.90; c is present in an amount that ranges from greater than 0 to 0.20; d is present in an amount that ranges from 0.0000001 to 0.20; e is present in an amount that ranges from greater than 0 to 0.20; f is present in an amount that ranges from greater than 0 to 0.80; and g is present in an amount that ranges from greater than 0.05 to 0.90;

wherein the numerical values of a, b, c, d, e, f, and g represent the relative gram-atom ratios of the elements in the catalyst.

Aspect 9: The catalyst according to any one of aspects 1-8, wherein the product comprises acetic acid, acrylic acid, or propanoic acid, or a combination thereof.

Aspect 10: The catalyst composition according to any one of aspects 1-9, wherein the catalyst converts the propylene to the product comprising the carboxylic acid moiety in a single stage.

Aspect 11: A method for the conversion of a propylene to a product comprising a carboxylic acid moiety, wherein the method comprises:

contacting the propylene with a catalyst, wherein the catalyst comprises:

MoVGaPdNbXY, wherein
   X comprises La, Te, Ge, Zn, In, or W; and
   Y comprises Al or Si;
wherein
   one or more Mo, V, Ga, Pd, Nb, La, Te, Ge, Zn, In, W, Al,
   and/or Si are optionally present in combination with oxygen.

Aspect 12: The method according to aspect 11, wherein the catalyst does not comprise an additional element that acts as a catalyst in the conversion of the propylene to the product.

Aspect 13: The method according to any one of aspects 11-12, wherein the catalyst comprises

$$Mo_aV_bGa_cPd_dNb_eX_fY_g$$

wherein a is 1; b is present in an amount that ranges from 0.01 to 0.90; c is present in an amount that ranges from greater than 0 to 0.20; d is present in an amount that ranges from 0.0000001 to 0.20; e is present in an amount that ranges from greater than 0 to 0.20; f is present in an amount that ranges from greater than 0 to 0.80; and g is present in an amount that ranges from greater than 0 to 0.90;

wherein the numerical values of a, b, c, d, e, f, and g represent the relative gram-atom ratios of the elements in the catalyst.

Aspect 14: The method according to any of aspects 11-13, wherein the product comprises acetic acid, acrylic acid, or propanoic acid, or a combination thereof.

Aspect 15: The method according to any of aspects 11-14, wherein the method does not comprise an additional catalyst.

Aspect 16: The method according to any of aspects 11-15, wherein the method comprises a single stage process with a single catalyst.

Aspect 17: The method according to any of aspects 11-16, wherein the product does not comprise substantially any acrolein.

Aspect 18: The method according to any of aspects 11-17, wherein the product does not comprise any acrolein.

Aspect 19: The method according to any of aspects 11-18, wherein the catalyst is present on a support.

Aspect 20: The method according to any of aspects 11-19, wherein the catalyst consists essentially of MoVGaPdNbXY.

E. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Methods for preparing the catalysts of this invention and their use in the oxidation of propylene are illustrated in the following examples. Starting materials and the requisite intermediates are in some cases commercially available, or can be prepared according to literature procedures or as illustrated herein.

The catalyst was prepared by the following general procedure:

Aqueous solutions of vanadium and molybdenum were prepared separately. The vanadium solution was mixed with the molybdenum solution at a specified temperature and pH. The remaining required components were slowly added to the combined gel solution. After mixing, the resultant gel was dried to incipient wetness with continuous stirring.

After drying the resultant gel mixture at about 120° C. for about 16 hours, the resultant catalyst was heated to about 350° C. at a rate of about 2° C. per minute and calcined at this temperature in air for 4 hours to produce the desired oxide composition.

The Examples are provided herein to illustrate the invention, and should not be construed as limiting the invention in any way.

Example 1

Preparation of [$Mo_1V_{0.398}Ga_{1.0E-05}Pd_{1.90E-04}Nb_{0.125}Te_{0.23}Al_{0.23}$]

Ammonium metavanadate (Aldrich Chemicals, Assay=99.0%) in the amount of 7.6 g was added to 80 mL of distilled water and heated to 90° C. with stirring. A yellow color solution with pH between 5 and 6 was obtained (Solution A). Niobium hydrate oxide (3.4 g, 80% $Nb_2O_5$, Niobium Products Company, USA) and 20 g of oxalic acid were added to 80 mL of water and heated to 95° C. with continuous stirring to give a clear solution with a pH of 0.57 (Solution B). Solution A and B were mixed together at 90° C. with continuous stirring. During the addition, color changes from pale yellow to brown to green to dark green were observed. The pH of the solution was 1.20 at 85° C. A dark blue-green color solution with a pH of 1 at 90° C. was obtained (Solution C). Ammonium paramolybdate tetrahydrate (Aldrich Chemicals A.C.S—12054-85-2) in the amount of 28.8 g was added to 30 mL of water and heated to 60° C. to give a colorless solution with a pH between 5.0 and 6.0 (Solution D). Solution D was combined slowly with Solution C to give dark blue to dark gray color precipitates (Mixture E). Required amounts of palladium followed by telluric acid and gallium oxide, and alumina were added slowly to gel mixture. This dark color combination was stirred vigorously to achieve a homogeneous gel mixture which was then slowly dried to incipient dryness with continuous stirring.

The resulting solid was put in a China dish and dried additionally in an oven at 120° C. for 16 hours. The dried material was cooled to room temperature and placed in a furnace. Catalyst was calcined from 300 to 600° C. for 4 to 8 hours.

Calcined catalyst was formulated into uniform particles of the 40-60 mesh size and evaluated for the propylene oxidation reaction.

Example 2

Catalyst Testing: Oxidation of Propylene

Catalyst prepared as in Example 1 was evaluated at a temperature of 300° C. with feed mixture containing propylene:oxygen:nitrogen (3:6:91). Catalyst evaluation was carried out in a stainless steel fixed bed tubular reactor under standard process conditions. Gas feed composition used for the evaluation of this catalyst contained propylene, oxygen and nitrogen (water). The reaction was carried out at a temperature of 300° C. to 330° C., a pressure of 15 psia and at a space velocity of about 1,090 h$^{-1}$ using 40-60 mesh calcined catalyst.

Reaction products were analyzed on-line by gas chromatography. Oxygen, argon and carbon monoxide were analyzed using a 2.5 m by 3 mm column of 13× molecular sieve. Carbon dioxide and, propylene were analyzed using a 2 m by 3 mm column packed with material sold under the trade name HayeSep Q® (Hayes Separation Inc.). Liquids products (acrylic acid, acrolein, acetic acid and water) were analyzed using a 2 m by 3 mm column packed with material sold under the trademark PORAPAK QS™ (Waters Corporation). In all cases, the conversion and selectivity calculations were based on the reaction stoichiometry.

Analysis of the reaction products showed the following results:

TABLE 1

| Product | Conversion % | Selectivity % |
|---|---|---|
| Propylene | 70 | |
| Oxygen | 80 | |
| Acrylic acid | | 60 |
| Acetic acid | | 12 |
| COx (x = 1 or 2) | | 23 |
| Propanoic acid | | 5 |
| Acrolein | | 0 |

Overall, the recycle yield for acrylic acid and acetic acid was 72%, where 83% was acrylic acid and no acrolein was found in the product.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A catalyst for the conversion of propylene to a product comprising a carboxylic acid moiety, wherein the catalyst comprises:

MoVGaPdNbXY, wherein
    X is La, Te, Ge, Zn, In, or W; and
    Y is Al or Si;
    wherein
    one or more of Mo, V, Ga, Pd, Nb, La, Te, Ge, Zn, In, W, Al, and/or Si are optionally present in combination with oxygen;
    wherein the product does not comprise substantially any acrolein.

2. The catalyst of claim 1, wherein the product does not comprise any acrolein.

3. A catalyst for the conversion of propylene to a product comprising a carboxylic acid moiety, wherein the catalyst consists essentially of:

MoVGaPdNbXY, wherein
    X is La, Te, Ge, Zn, In, or W; and
    Y is Al or Si;
    wherein
    Mo, V, Ga, Pd, Nb, La, Te, Ge, Zn, In, W, Al, and/or Si are optionally present in combination with oxygen; and
    wherein the product does not comprise substantially any acrolein.

4. The catalyst of claim 3, wherein the catalyst is present on a support.

5. The catalyst of claim 3, wherein the catalyst comprises:

$Mo_aV_bGa_cPd_dNb_eX_fY_g$ wherein a is 1; b is present in an amount that ranges from 0.01 to 0.90; c is present in an amount that ranges from greater than 0 to 0.20; d is present in an amount that ranges from 0.0000001 to 0.20; e is present in an amount that ranges from greater than 0 to 0.20; f is present in an amount that ranges from greater than 0 to 0.80; and g is present in an amount that ranges from greater than 0.50 to 0.90;
    wherein the numerical values of a, b, c, d, e, f, and g represent the relative gram-atom ratios of the elements in the catalyst.

6. The catalyst of claim 3, wherein the product comprises acetic acid, acrylic acid, or propanoic acid, or a combination thereof.

7. The catalyst composition of claim 3, wherein the catalyst converts the propylene to the product comprising the carboxylic acid moiety in a single stage.

8. A method for the conversion of propylene to a product comprising a carboxylic acid moiety, wherein the method comprises:

contacting the propylene with a catalyst, wherein the catalyst comprises:

MoVGaPdNbXY, wherein
    X is La, Te, Ge, Zn, In, or W; and
    Y is Al or Si;
    wherein
    Mo, V, Ga, Pd, Nb, La, Te, Ge, Zn, In, W, Al, and/or Si are optionally present in combination with oxygen; and wherein the product does not comprise substantially any acrolein.

9. The method of claim 8, wherein the product comprises acetic acid, acrylic acid, or propanoic acid, or a combination thereof.

10. The method of claim 8, wherein the method does not comprise an additional catalyst.

11. The method of claim 8, wherein the method comprises a single stage process with a single catalyst.

12. The catalyst of claim 1, wherein the catalyst is present on a support.

13. The catalyst of claim 1, wherein the catalyst comprises:

$Mo_aV_bGa_cPd_dNb_eX_fY_g$ wherein a is 1; b is present in an amount that ranges from 0.01 to 0.90; c is present in an amount that ranges from greater than 0 to 0.20; d is present in an amount that ranges from 0.0000001 to 0.20; e is present in an amount that ranges from greater than 0 to 0.20; f is present in an amount that ranges from greater than 0 to 0.80; and g is present in an amount that ranges from greater than 0.50 to 0.90;
    wherein the numerical values of a, b, c, d, e, f, and g represent the relative gram-atom ratios of the elements in the catalyst.

14. The catalyst of claim 1, wherein the product comprises acetic acid, acrylic acid, or propanoic acid, or a combination thereof.

15. The catalyst of claim 1, wherein the catalyst converts the propylene to the product comprising the carboxylic acid moiety in a single stage.

16. The catalyst of claim 1, wherein less than 1% of acrolein is formed in the product using the catalyst.

17. The catalyst of claim 3, wherein less than 1% of acrolein is formed in the product using the catalyst.

18. The method of claim 8, wherein less than 1% of acrolein is formed in the product using the catalyst.

* * * * *